United States Patent
Ko et al.

(10) Patent No.: US 10,413,843 B2
(45) Date of Patent: *Sep. 17, 2019

(54) CANNABINOID EXTRACTION AND DISTILLATION

(71) Applicant: NextLeaf Solutions Ltd., Vancouver (CA)

(72) Inventors: Ryan Delmoral Ko, Coquitlam (CA); Brock Hughes, Port Coquitlam (CA)

(73) Assignee: Nextleaf Solutions Ltd., Vancouver (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/993,457

(22) Filed: May 30, 2018

(65) Prior Publication Data

US 2019/0099695 A1 Apr. 4, 2019

Related U.S. Application Data

(63) Continuation of application No. 15/721,344, filed on Sep. 29, 2017, now Pat. No. 9,987,567.

(51) Int. Cl.
*B01D 11/02* (2006.01)
*B01D 15/00* (2006.01)
*B01D 3/08* (2006.01)
*B01D 3/40* (2006.01)
*C07C 37/86* (2006.01)
*C07C 37/00* (2006.01)
*C07D 311/80* (2006.01)

(52) U.S. Cl.
CPC ......... *B01D 11/0288* (2013.01); *B01D 3/085* (2013.01); *B01D 3/40* (2013.01); *B01D 11/028* (2013.01); *B01D 15/00* (2013.01); *C07C 37/004* (2013.01); *C07C 37/86* (2013.01); *C07D 311/80* (2013.01)

(58) Field of Classification Search
CPC .... B01D 11/0288; B01D 3/085; B01D 15/00; B01D 11/028; B01D 3/40; C07C 37/004; C07C 37/86; C07D 311/80
See application file for complete search history.

(56) References Cited

U.S. PATENT DOCUMENTS

| | | | |
|---|---|---|---|
| 7,700,368 B2 | 4/2010 | Flockhart et al. | |
| 9,155,767 B2 * | 10/2015 | Hospodor | A61K 36/185 |
| 9,649,349 B1 * | 5/2017 | Tucker | B01D 3/02 |
| 9,655,937 B2 * | 5/2017 | Jones | B01D 11/0219 |
| 9,744,200 B1 | 8/2017 | Tucker | |
| 9,987,567 B1 * | 6/2018 | Ko | C07C 37/004 |
| 10,351,937 B2 * | 7/2019 | Kawata | C22C 38/38 |
| 2013/0079531 A1 * | 3/2013 | Barringer | C07D 311/78 |
| | | | 549/390 |
| 2014/0330030 A1 | 11/2014 | Ferri | |
| 2015/0126754 A1 | 5/2015 | Fernandez Cid | |
| 2017/0106030 A1 | 4/2017 | Aari | |
| 2018/0362429 A1 * | 12/2018 | Zhang | C07C 37/82 |
| 2018/0369715 A1 * | 12/2018 | Bruining | A61K 36/185 |

FOREIGN PATENT DOCUMENTS

| | | |
|---|---|---|
| WO | 2004016277 | 2/2004 |
| WO | 2013165251 | 11/2013 |
| WO | 2016123475 | 8/2016 |

OTHER PUBLICATIONS

Romano, L. L.,"Cannabis oil: chemical evaluation of an upcoming cannabis-based medicine." Cannabinoids 1.1 (2013): 1-11.*
Canadian Intellectual Property Office Examination Report dated Nov. 20, 2018 issued for the co-pending Canadian application assigned Application No. 3,016,078 with an International Filing Date of Aug. 31, 2018.
European Patent Office Search Report dated Feb. 20, 2019 issued for the co-pending European application assigned Application No. EP18196360.4.
Canadian Intellectual Property Office Examination Report dated Feb. 1, 2019 issued for the co-pending Canadian application assigned Application No. 3,016,078 with a Filing Date of Aug. 31, 2018.

* cited by examiner

*Primary Examiner* — John M Mauro
(74) *Attorney, Agent, or Firm* — Damien G. Loveland

(57) ABSTRACT

Raw plant material is mixed with ethanol under pressure to extract essential elements. The resulting crude oil and ethanol with the dissolved essential elements is separated from the raw plant material and filtered to remove particulates, waxes, lipids, fats and dissolved impurities. The ethanol is then evaporated from the resulting mixture of crude oil and ethanol, and the remaining crude oil then undergoes decarboxylation and distillation to obtain the essential elements. The ethanol may be chilled before adding it to the raw plant material.

19 Claims, 3 Drawing Sheets

CANNABINOID EXTRACTION AND DISTILLATION

TECHNICAL FIELD

This application relates to the extraction of essential elements from plant material. More specifically, it relates to the extraction of cannabinoids from *cannabis* plants.

BACKGROUND

In legal, adult-use markets, sales of extracts are growing ten times faster compared to the sales of dried *cannabis*, and extracts account for over 60% of revenue. With legalization, consumer preferences are shifting from dried *cannabis* to extracted *cannabis* products.

However, the scent and flavors of *cannabis* can be undesirable in many infused products because of excess lipids, plant matter and impurities present in currently available extracts.

U.S. Pat. No. 9,155,767 to Hospodor et al. relates to the extraction of medicinal *cannabis* compounds into an eluate, by separating a portion of medicinal *cannabis* compounds contained within a portion of eluate at a first extraction target level, to provide enough clean solvent to continue extraction operations. A high efficiency concentrator processes eluate from one or more tanks, creating clean solvent when extraction targets are met or when clean solvent is exhausted. This manages eluate concentration levels and limits the quantity of concentrated medicinal *cannabis* compounds on site at any moment in time.

This background information is provided to reveal information believed by the applicant to be of possible relevance to the present invention. No admission is necessarily intended, nor should be construed, that any of the preceding information constitutes prior art against the present invention.

SUMMARY OF INVENTION

The present invention is directed to the extraction of essential elements from plant material, and in particular it relates to the extraction of cannabinoids from *cannabis* plants by dissolving them in solution under pressure, followed by filtration, evaporation, decarboxylation and distillation. Ethanol used as the solvent may be chilled before adding it to the raw plant material.

As disclosed, an aspect of the present invention is a process for extracting essential elements from raw plant material comprising: drying raw plant material; grinding the raw plant material to result in ground raw plant material; adding ethanol to the ground raw plant material to form a mixture; pressurizing the mixture; removing solid ground raw plant material from the mixture to leave a crude oil and ethanol mixture; filtering the crude oil and ethanol mixture to remove unwanted components; evaporating ethanol from the filtered crude oil and ethanol mixture to leave crude oil; decarboxylating the crude oil to leave a first residue; subjecting the first residue to a first film wipe to remove volatile terpenes and leave a second residue; subjecting the second residue to a second film wipe to remove non-volatile terpenes and leave a third residue; and subjecting the third residue to a third film wipe to obtain essential elements.

In some embodiments, the raw plant material is dried to 0-15% moisture content; the raw plant material is ground to an average size of 250-5000 µm; the ethanol is added to the ground raw plant material in a ratio of 1 liter of ethanol to 1 kg of ground raw plant material; and the mixture is pressurized to pressure of 70-280 kPa.

In some embodiments, filtering the crude oil and ethanol mixture comprises: adding charcoal particles to the crude oil and ethanol mixture; agitating the charcoal particles and crude oil and ethanol mixture; filtering off the charcoal particles; adding clay particles to the crude oil and ethanol mixture; agitating the clay particles and crude oil and ethanol mixture; filtering off the clay particles; adding silica particles to the crude oil and ethanol mixture; agitating the silica particles and crude oil and ethanol mixture; and filtering off the silica particles.

In some embodiments, filtering off the charcoal particles comprises filtering the charcoal particles and crude oil and ethanol mixture with a 10-30 µm filter and then with an 0.25-1 µm filter; filtering off the clay particles comprises filtering the clay and crude oil and ethanol mixture with a second 10-30 µm filter and then with a second 0.25-1 µm filter; and filtering off the silica particles comprises filtering the silica particles and crude oil and ethanol mixture with a third 10-30 µm filter and then with a third 0.25-1 µm filter. In some embodiments, all the adding and agitating steps are carried out with the crude oil and ethanol mixture at a temperature of 60-78° C.; and all the filtering off steps are carried out with the crude oil and ethanol mixture at a temperature of 10-50° C.

BRIEF DESCRIPTION OF DRAWINGS

The following drawings illustrate embodiments of the invention, which should not be construed as restricting the scope of the invention in any way.

DESCRIPTION

A. Glossary

Cannabidiol (CBD) is one of the active cannabinoids found in *cannabis* and is used for medicinal purposes.

Cannabinoids are a group of chemicals that act on cannabinoid receptors in the body, numerous of which are found in the *cannabis* plant.

Crude oil is a term for the description of condensed, non-filtered oil, i.e. oil that is non-winterized and not treated via charcoal, clay and silica. The crude oil contains the essential elements.

Tetrahydrocannabinol (THC) is a psychotropic cannabinoid and is the main psychoactive ingredient of *cannabis*. THC also has medicinal uses. THCa is the non-psychoactive form of THC.

Rotovap—a rotary evaporator.

Winterization refers to the removal of unwanted plant waxes and lipids.

B. Overview

Figure 1:
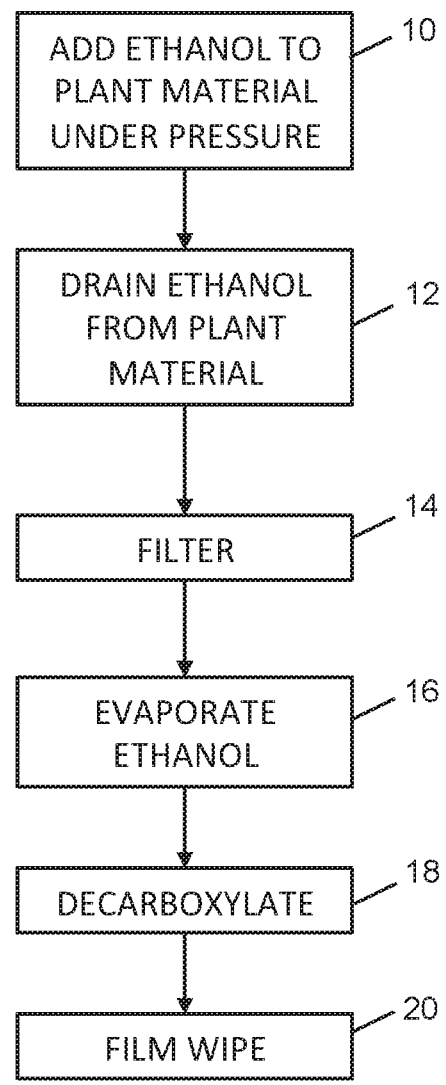
FIG. 1 is a high-level flowchart showing the key steps of a process for extracting cannabinoids according to an embodiment of the present invention.

Referring to FIG. 1, a flowchart of the basic steps of the process is shown. In step 10, a solvent such as ethanol is added to dried and ground plant material under pressure. The ethanol may be at room temperature or chilled. As a result, the essential elements found in the plant material dissolve into the ethanol. In step 12, the ethanol solution is drained from the plant material to form a crude oil and ethanol mixture. The first two steps are considered to be the primary extraction phase.

In step 14, impurities are then removed by filtration from the crude oil and ethanol mixture, which contains the essential elements. In step 16, ethanol is removed or reclaimed from the mixture, by evaporation, for example. Steps 14 and 16 are considered to be the solvent reclamation stage.

In step 18, the crude oil remaining after the evaporation is decarboxylated to activate the THC and evaporate any remaining solvent. The residue after decarboxylation is then, in step 20, distilled using a film wipe apparatus in order to extract the essential elements.

C. Exemplary Process

Figure 2:
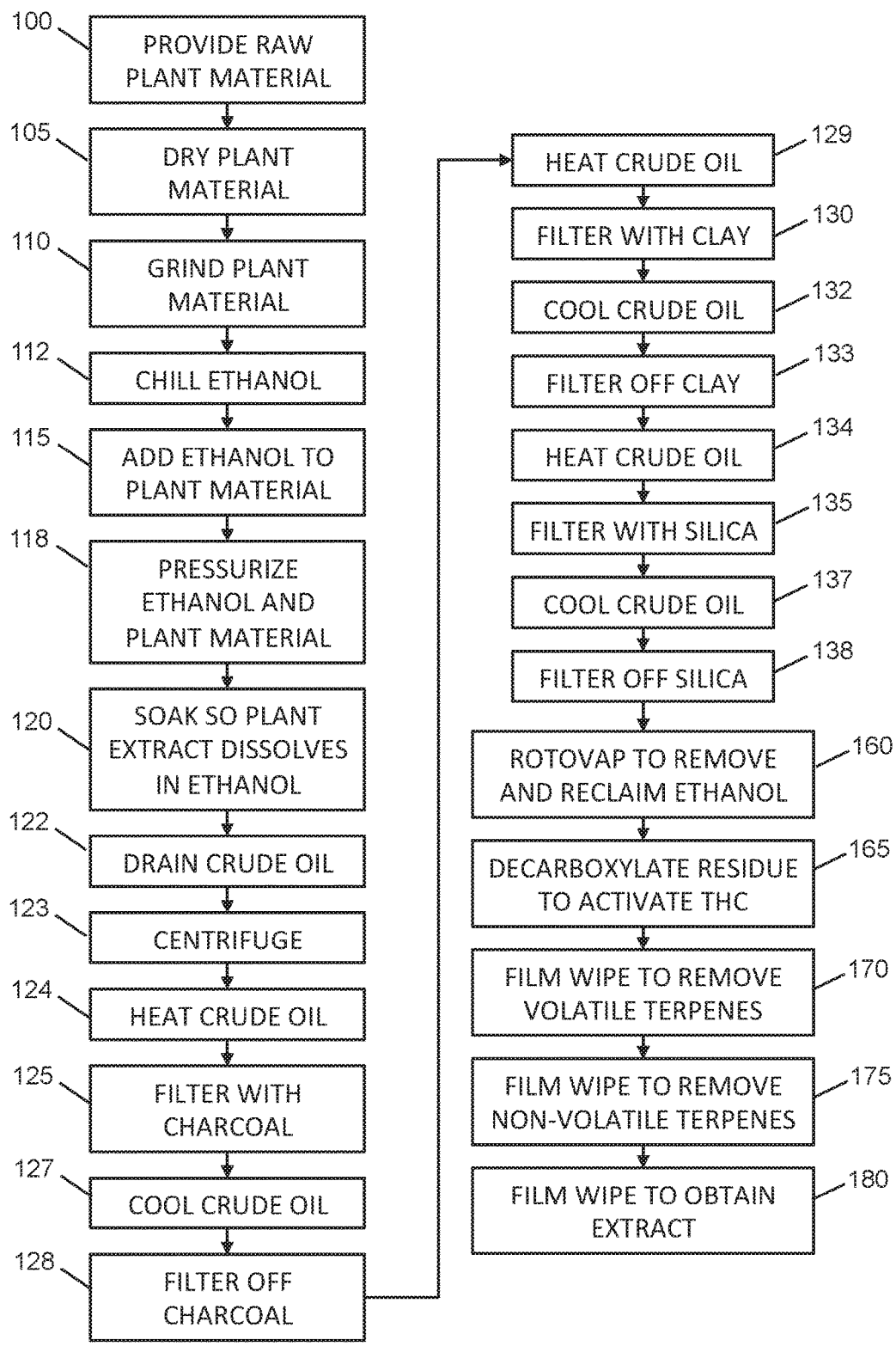
FIG. 2 is a flowchart showing more detailed steps of a process for extracting cannabinoids according to an embodiment of the present invention.

Referring to FIG. 2, a detailed process for the extraction of essential elements is shown. This exemplary process relates to the extraction of cannabinoids from *cannabis*.

Steps 100-123 relate to the primary extraction phase. Steps 124-138 relate to the filtration stage. The filtration stage and the rotovap stage 160 form the solvent reclamation phase. Step 165 relates to the decarboxylation stage, and steps 170-180 relate to the distillation of the cannabinoids.

In step 100, raw plant material is provided. The raw plant material includes, for example, the flower, the leaves and the stems close to the leaves. Any part of the plant that contains cannabinoid resin glands can be included. Not all stems and leaves have these glands present. In other cases, the raw plant material includes only the flowers. In still other cases, the raw plant material includes only the leaves and stems, i.e. the parts of the plant that would normally be considered waste, in which valuable phytochemicals are found only in lower concentrations.

In step 105, the raw plant material is dried, if it is not already provided in dried form. The raw plant material is dried in a dry room with a dehumidifier air controller, or it may be flash dried in a vacuum oven at a pressure of <2 kPa. Ideally, the moisture content of the raw plant material after drying is 10% or below, by weight. The temperature of the oven and the drying time depend on how much moisture the raw material has, and how much raw material there is. Moisture content is measured using a hygrometer or using high-performance liquid chromatography. The lower the moisture content is, the better, because lower moisture will cause less dilution of the ethanol than if the moisture level were higher. If the ethanol that is reclaimed is diluted with water, it will be less effective for repeat processes. Nevertheless, in other embodiments, the moisture content can be as high as 15% while still allowing for an acceptable process. In other embodiments, other drying techniques may be used.

In step 110, the dried plant material is ground, for example to an average size between 250-300 μm. However, it is possible in other embodiments to grind the dried plant material to a size of thousands of microns, and the process has been found to work with average particle sizes of up to 3000-5000 μm. If the plant material is ground to less than 250 μm, say, then problems occur with unwanted packing of the material in the material columns (240, FIG. 3). Notably, the unwanted packing is due to the raw material packing into a plug under applied pressure. If the particulate is too fine, the raw material will form a seemingly solid mass making it difficult for ethanol to pass through it.

Note that, in other embodiments, the grinding step may take place before the drying step.

In step 112, the ethanol is chilled to a temperature between −42° C. and −50° C., in a tank surrounded by a pressurized liquid $CO_2$ jacket, for example. In other embodiments, the ethanol is chilled using a heat exchanger or a jacket of solid $CO_2$ or liquid nitrogen.

In step 115, ethanol is added to the material column into which the ground and dried plant material has been placed. Typically, approximately 50 liters of ethanol is used for every 5 kg of plant material, although it is possible that other ratios can be used.

In some embodiments where the ethanol is chilled, the optimum temperature has been found to be −45° C. However, the optimum temperature may be different in other embodiments. The optimum choice is a compromise between keeping the time needed for chilling to a minimum, keeping the consumption of the liquid nitrogen and/or liquid $CO_2$ coolant down, and maximizing the miscibility of the ethanol with the essential elements that are to be extracted. Nevertheless, using the filtration process described herein, the fats and lipids can be removed economically from the extracted crude oil and ethanol mixture. The use of chilled ethanol is more efficient for the process in general with respect to post-filtration steps, however, it has slightly less efficiency with respect to yield. Non-chilled ethanol is more efficient in terms of extraction yield but very inefficient for post-filtration steps. Non-chilled ethanol extracts unwanted fats, waxes and lipids.

In step 118, the mixture of ethanol and plant material is pressurized to a pressure in the range of 70-280 kPa (10-40 psi). The aim is to select a pressure that is just low enough to prevent a plug of plant material forming within the material column. The actual value of the pressure is determined by the material column packing. The tighter the raw plant material is packed into the column, the lower is the upper pressure limit with which the ethanol can be driven through the column. While under pressure, the temperature of the mixture may vary by up to ±5° C., but it should not be allowed to rise above −40° C.

In step 120, the plant material is allowed to soak in the ethanol for a while in order to allow the essential elements to dissolve into it. Typically, the plant material soaks for 5 minutes provided that the temperature is below −40° C. In other embodiments, the soaking time may be different. The pressure is maintained in the range of 70-280 kPa (10-40 psi) while the mixture of ethanol and plant material is soaking.

In step 122, the ethanol, now with the crude oil and dissolved essential elements, is drained off from the bulk of the plant material, to form a mixture of crude oil and ethanol. This mixture is the total fluid that comes directly out of the extractor (material column) post-extraction. The crude oil contains essential elements and is dissolved in the ethanol. The mixture also contains some unwanted residual plant matter and other undesirable components. The crude oil and ethanol mixture is drained off under a pressure in the range of 70-280 kPa (10-40 psi), i.e. it is the same pressure as the pressure used to soak the plant material.

In other embodiments, the ethanol is pumped continuously through the raw plant material under pressure in the range of 70-280 kPa (10-40 psi), without the specific soaking step.

Optionally, in step 123, a centrifuge is used to separate the further plant material from the crude oil and ethanol mixture. The centrifuge may be used instead of the step 122 of draining of the material column, or instead of the pumping of ethanol through the raw material under pressure. In this case the contents of the material column are transferred into the centrifuge directly.

In step 124, the crude oil and ethanol mixture is heated to a temperature between 60° C. and 78° C. for filtering. It is important not to exceed the upper temperature of this range, because targeted elements in the crude oil will melt into the liquid state, and will be unable to be filtered out. Also, the ethanol will boil and there may be cannabinoid degradation. In other embodiments it is possible to omit this step and perform the subsequent filtration steps at room temperature or even using the crude oil and ethanol mixture in its previously chilled state, or at another chilled temperature, e.g. as low as −40° C.

In the following steps, the crude oil and ethanol mixture is filtered to remove further plant material that is unavoidably retained in the mixture during the draining step. Filtration removes fats, lipids, chlorophyll, waxes, heavy metals and other undesirable chemicals. Typically there are 1-5 different filters. While filtration is always required, the filtration steps required are not necessarily as robust if the ethanol used in the primary extraction phase is chilled, compared to if the ethanol is non-chilled.

In step 125, the crude oil and ethanol mixture is filtered through or with charcoal. The charcoal removes pigments, chlorophyll, heavy metals and particulates. Charcoal is used as the first filter medium in order to remove as much pigment as possible. The charcoal, when in particulate form, is first added to the heated crude oil and ethanol mixture and then the mixture is agitated. The average size of the charcoal particles is in the range 0.25-150 µm, although other sizes are possible in other embodiments.

The crude oil and ethanol mixture is then cooled, or allowed to cool to a temperature of between 10-50° C. in step 127. Any charcoal that is in the crude oil and ethanol mixture is removed by filtering it out using borosilicate glass filter paper, in step 128, particularly if it has been added to the crude oil and ethanol mixture during the filtration process. Filtering out the charcoal is done at a temperature of between 10-50° C. Other filter media or material, or a filter screen may be used instead. For example, the solution is filtered through a 10-30 µm paper filter or screen and then through an 0.25-1 µm paper filter or screen. In other embodiments, a different number of paper or screen filters can be used, and they can have different sizes.

In step 129, the crude oil and ethanol mixture is reheated to a temperature between 60° C. and 78° C. for further filtering. In other embodiments it is possible to omit this step and perform the subsequent filtration steps at room temperature or even using the crude oil and ethanol mixture in its previously chilled state, or at another chilled temperature, e.g. as low as −40° C.

In step 130, the crude oil and ethanol mixture is filtered through or with an agulite clay, also known as fuller's earth clay, palygorskite or attapulgite. The clay primarily removes pigments. The clay, when in particulate form, is first added to the heated crude oil and ethanol mixture and then the mixture is agitated. The average size of the clay particles is in the range 0.25-150 µm, although other sizes are possible in other embodiments.

The crude oil and ethanol mixture is then cooled, or allowed to cool to a temperature of between 10-50° C. in step 132. Any clay that is in the crude oil and ethanol mixture is removed by filtering it out in step 133, using borosilicate glass filter paper, particularly if it has been added to the crude oil and ethanol mixture during the filtration process. Other filter media or material, or a filter screen may be used instead. For example, the solution is filtered through a 10-30 µm paper filter or screen and then through an 0.25-1 µm paper filter or screen. In other embodiments, a different number of paper or screen filters can be used, and they can have different sizes.

In step 134, the crude oil and ethanol mixture is reheated to a temperature between 60° C. and 78° C. for still further filtering. In other embodiments it is possible to omit this step and perform the subsequent filtration steps at room temperature or even using the crude oil and ethanol mixture in its previously chilled state, or at another chilled temperature, e.g. as low as −40° C.

In step 135, the crude oil and ethanol mixture is then filtered through or with silica. The silica removes very fine plant matter and other particulates. The silica, when in particulate form, is first added to the heated crude oil and ethanol mixture and then the mixture is agitated. The average size of the silica particles is in the range 0.25-150 µm, although other sizes are possible in other embodiments. The removal very fine solid particulates helps the winterisation of the oil to occur faster. Additionally it allows for visibility of the product, which in turn allows one to review the integrity of the filtration process.

The crude oil and ethanol mixture is then cooled, or allowed to cool to a temperature of between 10-50° C. in step 137. Any silica that is in the crude oil and ethanol mixture is removed by filtering it out in step 138, using borosilicate glass filter paper, particularly if it has been added to the crude oil and ethanol mixture during the filtration process. Other filter media or material, or a filter screen may be used instead. For example, the solution is filtered through a 10-30 µm paper filter or screen and then through an 0.25-1 µm paper filter or screen. In other embodiments, a different number of paper or screen filters can be used, and they can have different sizes.

In step 160, the crude oil and ethanol mixture is then processed with a rotovap to remove and reclaim any ethanol that remains in it. The temperature of the rotovap is 43-49° C., and it is operated at a pressure of 83-101 kPa (25-30 inHg, 635-760 mmHg). Other evaporators may be used in other embodiments, for example, an Ecochyll II7 can be used. The ethanol that is reclaimed can be used to extract essential elements from a further batch of dried and ground raw plant material.

After the remaining ethanol has been removed using the rotovap, decarboxylation is performed on the resulting crude oil in step 165. The crude oil is heated to 120-140° C. in order to evaporate residual solvents and to convert THCa into THC, releasing $CO_2$ in the process. If the temperature is below this range, then potentially there will be some residual ethanol. The majority of the $CO_2$ that is produced from decarboxylation is removed in order to ensure consistent vacuum levels later on in the process. If the temperature is above this range, then product degradation occurs. The crude oil is warmed up gradually while stirring so as not to overheat portions of it. In the decarboxylation step the residual ethanol is not reclaimed. The decarboxylation process typically takes several hours.

Figure 3:
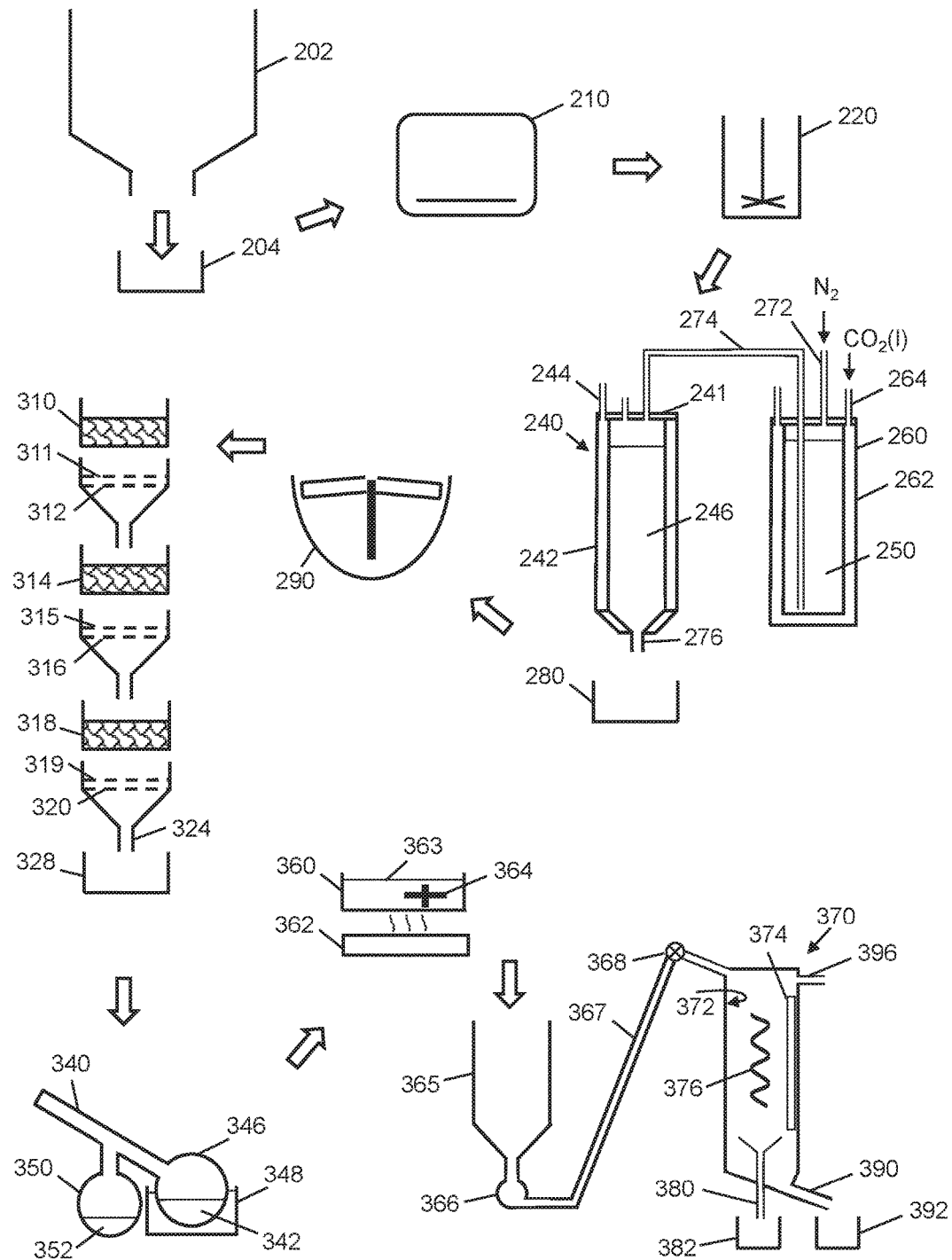
FIG. 3 is a schematic diagram of the apparatus used for the extraction of cannabinoids according to an embodiment of the present invention.

In step 170 and referring to FIG. 3, the decarboxylated crude oil is run through a short-path distillation film wipe apparatus 370. Since we are using a wiped film distillation process versus a conventional short path still apparatus it is important to have separated the waxes, fats and lipids pre-distillation. If this is not done, the waxes, fats and lipids will be wiped onto the wipe film causing the distillation of some of these elements into the final product.

The decarboxylated crude oil is first run through the short-path distillation film wipe apparatus to remove some volatile terpenes. The temperature of the feed tank 365 to the film wipe is set in the range 105-115° C., and is more usually set in the range 107-110° C. The temperatures of the pump 366 and feed line 367 to the film wipe are set at the same value as the feed tank. The temperature of the residue discharge arm 390 and its associated pump, not shown, is also set in the range 105-115° C., and is also more usually set in the range 107-110° C. The temperature of the target heater, which controls the temperature of the inner wall 372, is set within a range of 155-162° C., usually 159.5° C. The condensing coil 376 is set at a temperature of 58° C., as is the target or distillate discharge arm 380 and its associated pump (not shown). A further temperature control unit maintains the temperature of a cold trap between the vacuum port 396 and the vacuum pump at −22 to −30° C., although even cooler temperatures are possible. The film-wipe process is performed at a pressure of 0.3-0.8 mbar.

In step 175, the residual crude oil, after volatile terpene removal, is re-run through the short-path distillation film wipe to remove some non-volatile terpenes. All of the temperatures are the same except for the temperature of the inner wall, which is typically set to a higher temperature and is in the range 159-162° C. The pressure is the same, at 0.3-0.8 mbar.

In step 180, the further residual crude oil is again run through the short-path distillation film wipe to remove the cannabinoids as a whole. The temperature of the feed tank 365 to the film wipe is set in the range 105-115° C., and is more usually set in the range 107-110° C. The temperatures of the pump 366 and feed line 367 to the film wipe are set at the same value as the feed tank. The temperature of the residue discharge arm 390 and its associated pump, not shown, is also set in the range 105-115° C., and is also more usually set in the range 107-110° C. The temperature of the target heater, which controls the temperature of the inner wall 372, is set within a range of 168.5-170° C. The condensing coil 376 is set at a temperature of 74° C., as is the target or distillate discharge arm 380 and its associated pump (not shown). The temperature of the cold trap between the vacuum port 396 and the vacuum pump is −22 to −30° C., although even cooler temperatures are possible. The film-wipe process is performed at a pressure of 0.03-0.08 mbar.

The result from the distillate discharge arm is a tasteless, odourless oil that contains up to 99% pure cannabinoids. Often, however, the further residual crude oil will require another pass through the wiped-film apparatus in order to achieve purities of 90% and over.

Using this process, a given weight of dried *cannabis* can be turned into very approximately 10-15% crude oil, which yields anywhere from 4-10% pure cannabinoids, again very approximately.

D. Alternate Process

In some embodiments the ethanol is not chilled in step 112, which is omitted, and the ethanol added to the raw plant material at room temperature (15-25° C.) in step 115. In these embodiments, steps 127, 132 and 137 are omitted, as the ethanol is not chilled before paper filter stages 118, 133 and 138. Filtration is particularly important if the ethanol is used at room temperature. It has been found that 15% more extracts are obtained using room-temperature ethanol compared to using chilled ethanol, but that the filtration stage is significantly more onerous. This is also subjective to the type of plant material used, but it is known that non-chilled ethanol has a greater miscibility, which makes the ethanol less discriminative thus picking up more unwanted materials.

E. Apparatus

Referring to FIG. 3, an example of the apparatus is shown schematically.

Raw plant material is provided in a hopper 202, for example, and is released in batches into container 204. The raw plant material is dried in vacuum oven 210. Next, the dried plant material is placed into a grinder 220, for example a Quadro Comil™ grinder.

After the grinding step, the ground plant material is placed into one or more material columns 240. Each column has a lid 241 that is removable so that the ground plant material can be placed into it. Each column holds 1.5-4.5 kg (3-10 lb) of plant material depending on its size. Other capacities are also possible. In one example apparatus, there are four material columns 240. The material column may be surrounded by an insulating wall or vacuum jacket 242, which can be evacuated via port 244. Alternately, an insulating jacket may be wrapped around the material column. The insulating wall 242 or jacket helps to maintain the contents 246 cool in the process that uses chilled ethanol as the solvent. When using chilled ethanol, the material column is maintained chilled by the use of pressurized, liquid $CO_2$ in the jacket.

The ethanol 250 is cooled in a cryogenic tank 260, the inner temperature of which is maintained low by a jacket 262 filled with pressurized liquid $CO_2$ via port 264. In other embodiments, other refrigerants can be used, or a chiller or heat exchanger can be used.

Pressurized nitrogen gas is fed into the port 272, forcing the chilled ethanol 250 through insulated tube 274 into the material column 240. The pressure of the nitrogen is used to maintain the pressure of the mixture 246 of ethanol and raw plant material, and/or to pump the ethanol through the raw plant material.

After the raw plant material has soaked in the ethanol, the ethanol, now with dissolved essential elements, is drained out of the material column 240 as a mixture of crude oil and ethanol, via outlet pipe 276 into container 280. The bulk of the raw plant material remains in the material column 240. The crude oil and ethanol mixture may alternately be pumped out of the material column under the pressure of the nitrogen.

Optionally, a centrifuge 290 is used to separate the bulk of the plant material from the mixture. If the centrifuge 290 is used, the contents of the material column are emptied into the centrifuge, which then separates the bulk of the plant material from the crude oil and ethanol mixture. The centrifuge 290 may be used instead of the draining of the material column, or instead of the pumping of ethanol through the raw material under pressure, or it may be used as well as the draining and/or pumping steps. As an example, the model CUP15 from Delta Separations LLC is a suitable centrifuge.

The crude oil and ethanol mixture is then fed into multiple different filters sequentially. In this embodiment, the first filter is charcoal 310. Below the charcoal there is a 10-30 µm filter 311 and an 0.25-1 µm filter 312 for filtering out charcoal. Next there is a clay filter 314, below which is a 10-30 µm filter 315 and an 0.25-1 µm filter 316 for filtering out the clay. Following this is a silica filter 318, below which is a 10-30 µm filter 319 and an 0.25-1 µm filter 320 for filtering out the silica. Each of the filters can be independently replaced. In other embodiments, the filters may be configured as a stack. After filtration, the crude oil and ethanol mixture leaves the final filter via exit pipe 324 and is collected in container 328.

The filtered crude oil and ethanol mixture is then passed into a rotovap 340. The crude oil and ethanol mixture 342 is maintained at an elevated temperature in flask 346, which is heated in a temperature bath 348. Flask 350 collects the ethanol 352, which is evaporated from the crude oil and ethanol mixture 342.

After the ethanol 352 has been reclaimed from the crude oil 342, the crude oil is decarboxylated in container 360, which is heated by heater 362. During the decarboxylation process, the crude oil 363 is stirred by a magnetic stirrer 364. After decarboxylation, the crude oil 363 is transferred to a feed chamber 365. At the bottom of the feed chamber 365, a pump 366 pumps the crude oil via a feed line 367 and a check valve 368 into a short-path film wipe apparatus 370. Pump rates are typically 1000-1500 ml/hr, and depend on the $CO_2$ being given off, if any, the percentage of THCa converted to THC, and the vacuum pressure of the short-path film wipe apparatus. In the short-path film wipe apparatus 370, the crude oil is wiped in a thin film around the heated, inside wall 372 of the film wipe apparatus 370 by a blade 374. The inside wall 372 is heated via a temperature-maintained jacket. A cooler, condensing coil 376 condenses the target fraction, which leaves the film wipe apparatus 370 as a distillate via target discharge tube 380 and is collected in container 382. The residual liquids fall down the inside wall 372 of the film wipe 370 and exit through residual arm 390 to be collected in container 392. The film wiping occurs under reduced pressure provided by a vacuum pump connected to port 396 via a cold trap.

Using the system of the present invention it is possible to convert approximately 36 kg (80 lb) of raw plant material into pure or nearly pure distillate oil over a period of 12 hours. The apparatus and process may also be used for the extraction, refinement and distillation of waste plant material from processes that do not succeed in extracting all the valuable extracts. The apparatus and process may be scaled up depending on the amount of raw plant material to be treated.

E. Variations

While the best presently contemplated mode of carrying out the subject matter disclosed and claimed herein has been described, other modes are also possible.

Optionally, once the cannabinoids have been extracted in step 180, they may be further run through the film wipe 370 in order to separate them into THC and CBD.

In other embodiments within the purview of the present invention, other plant materials besides *cannabis* may be processed. For example, hemp may be processed to result in a 95% pure CBD oil. The present invention has wide application in respect of other plants that produce phytochemicals of interest, such as for the extraction of essential elements from lavender. Phytochemicals of interest include cannabinoids, terpenes, and flavonoids.

In some embodiments, the apparatus is portable so that it can be taken to the different sites of various plant growers, to be used on an as-needed basis.

In general, unless otherwise indicated, singular elements may be in the plural and vice versa with no loss of generality.

Temperatures that have been given to the nearest degree include all temperatures within a range of ±0.5° C. of the given value. Temperatures that have been given to the nearest 0.1° C. include all temperatures within a range of ±0.05° C. of the given value.

Throughout the description, specific details have been set forth in order to provide a more thorough understanding of the invention. However, the invention may be practiced without these particulars. In other instances, well known elements have not been shown or described in detail and repetitions of steps and features have been omitted to avoid unnecessarily obscuring the invention. For example, various pumps, valves, jackets and lines are not shown for clarity. Accordingly, the specification and drawings are to be regarded in an illustrative, rather than a restrictive, sense.

It will be clear to one having skill in the art that further variations to the specific details disclosed herein can be made, resulting in other embodiments that are within the scope of the invention disclosed. Steps in the flowchart may be performed in a different order, other steps may be added, or one or more may be removed without altering the main outcome of the process. All parameters, dimensions, materials, and configurations described herein are examples only and may be changed depending on the specific embodiment. Accordingly, the scope of the invention is to be construed in accordance with the substance defined by the following claims.

The invention claimed is:

1. A process for extracting cannabinoids from raw *cannabis* plant material comprising the steps of:
   drying raw *cannabis* plant material;
   grinding the raw *cannabis* plant material to result in ground plant material;
   placing the ground plant material in a material column;
   adding ethanol to the ground plant material to form a mixture in the material column;
   pressurizing the mixture in the material column to a pressure of 70-280 kPa;
   removing solid ground plant material from the mixture to leave a crude oil and ethanol mixture;
   filtering the crude oil and ethanol mixture to remove unwanted components, wherein the filtering comprises the steps of:
      adding charcoal particles to the crude oil and ethanol mixture, agitating the charcoal particles and crude oil and ethanol mixture, and filtering off the charcoal particles; then
      adding clay particles to the crude oil and ethanol mixture, agitating the clay particles and crude oil and ethanol mixture, and filtering off the clay particles; and then
      adding silica particles to the crude oil and ethanol mixture, agitating the silica particles and crude oil and ethanol mixture, and filtering off the silica particles;
   evaporating ethanol from the filtered crude oil and ethanol mixture to leave crude oil;
   heating the crude oil to convert THCa in the crude oil into THC (tetrahydrocannabinol), resulting in decarboxylated crude oil; and
   distilling the decarboxylated crude oil to remove volatile and non-volatile terpenes therefrom and to obtain cannabinoids.

2. The process of claim 1, wherein cannabinoids in the raw *cannabis* plant material dissolve in the ethanol in the mixture.

3. The process of claim 1, wherein the solid ground plant material is removed from the mixture by centrifuging the mixture.

4. The process of claim 1, wherein the unwanted components are one or more of pigments, chlorophyll, fats, waxes, lipids, heavy metals and particulates.

5. The process of claim 1, further comprising subjecting the obtained cannabinoids to a film wipe distillation to separate the obtained cannabinoids into cannabidiol and tetrahydrocannabinol.

6. The process of claim 1, wherein the distilling step comprises:
   subjecting the decarboxylated crude oil to a first film wipe to remove the volatile terpenes and leave a first residue;
   subjecting the first residue to a second film wipe to remove the non-volatile terpenes and leave a second residue; and
   subjecting the second residue to a third film wipe to obtain the cannabinoids.

7. The process of claim 6, wherein:
   the first film wipe is performed with:
      a feed temperature of 105-115° C.;
      a residue discharge arm temperature of 105-115° C.;
      an inner wall temperature of 155-162° C.; and
      a condensing coil temperature of 58° C.;
   the second film wipe is performed with:
      a feed temperature of 105-115° C.;
      a residue discharge arm temperature of 105-115° C.;
      an inner wall temperature of 159-162° C.; and
      a condensing coil temperature of 58° C.; and
   the third film wipe is performed with:
      a feed temperature of 105-115° C.;
      a residue discharge arm temperature of 105-115° C.;
      an inner wall temperature of 168.5-170° C.; and
      a condensing coil temperature of 74° C.

8. The process of claim 1, wherein the heating step removes residual ethanol from the crude oil.

9. The process of claim 1, wherein the ethanol has been reclaimed from use in a prior process for extracting cannabinoids from raw *cannabis* plant material.

10. The process of claim 1, wherein the raw *cannabis* plant material is *cannabis* flower.

11. The process of claim 1, wherein the raw *cannabis* plant material is *cannabis* leaves and stems.

12. The process of claim 1, wherein the step of grinding occurs before the step of drying.

13. The process of claim 1, wherein the ethanol is at a temperature of −40° C. to −50° C. when it is added to the ground raw *cannabis* plant material.

14. The process of claim 13, wherein the mixture is left to soak for 5 minutes at a temperature of ≤−40° C. before the solid ground raw *cannabis* plant material is removed from the mixture.

15. The process of claim 1, wherein:
   the raw *cannabis* plant material is dried to 0-15% moisture content;
   the raw *cannabis* plant material is ground to an average size of 250-5000 μm; and
   the ethanol has a volume of x liters and to the ground plant material has a mass of x kg.

16. The process of claim 1, wherein the clay is an agulite clay.

17. The process of claim 1, wherein the evaporating step comprises subjecting the filtered crude oil and ethanol mixture to rotary evaporation at a temperature of 43-49° C. and a pressure of 83-101 kPa.

18. The process of claim 1, wherein the crude oil is heated to a temperature of 120-140° C.

19. A process for extracting cannabinoids from raw *cannabis* plant material comprising the steps of:
   drying raw *cannabis* plant material;
   grinding the raw *cannabis* plant material to result in ground plant material;
   placing the ground plant material in a material column;
   adding ethanol to the ground plant material to form a mixture in the material column;
   pressurizing the mixture in the material column to a pressure of 70-280 kPa;
   removing solid ground plant material from the mixture to leave a crude oil and ethanol mixture;
   filtering the crude oil and ethanol mixture to remove unwanted components;
   evaporating ethanol from the filtered crude oil and ethanol mixture to leave crude oil;
   heating the crude oil to convert THCa in the crude oil into THC (tetrahydrocannabinol), resulting in decarboxylated crude oil; and
   distilling the decarboxylated crude oil to remove volatile and non-volatile terpenes therefrom and to obtain cannabinoids, wherein the distilling step comprises:
      subjecting the decarboxylated crude oil to a first film wipe to remove the volatile terpenes and leave a first residue, wherein the first film wipe is performed with a feed temperature of 105-115° C., a residue discharge arm temperature of 105-115° C., an inner wall temperature of 155-162° C., and a condensing coil temperature of 58° C.;
      subjecting the first residue to a second film wipe to remove the non-volatile terpenes and leave a second residue, wherein the second film wipe is performed with a feed temperature of 105-115° C., a residue discharge arm temperature of 105-115° C., an inner wall temperature of 159-162° C., and a condensing coil temperature of 58° C.; and
      subjecting the second residue to a third film wipe to obtain the cannabinoids, wherein the third film wipe is performed with a feed temperature of 105-115° C., a residue discharge arm temperature of 105-115° C., an inner wall temperature of 168.5-170° C., and a condensing coil temperature of 74° C.

* * * * *